United States Patent [19]
Kossila

[11] Patent Number: 5,737,388
[45] Date of Patent: Apr. 7, 1998

[54] DIGITAL INTRAORAL X-RAY PHOTOGRAPHY METHOD AND HOLDER FOR PICTURE PLATE OR X-RAY FILM

[76] Inventor: Pauli Juhani Kossila, Ylioppilaskylä 6 B 11, FIN-20540 Turku, Finland

[21] Appl. No.: 702,527

[22] PCT Filed: Mar. 1, 1995

[86] PCT No.: PCT/FI95/00118

§ 371 Date: Oct. 11, 1996

§ 102(e) Date: Oct. 11, 1996

[87] PCT Pub. No.: WO95/23554

PCT Pub. Date: Sep. 8, 1995

[30] Foreign Application Priority Data

Mar. 3, 1994 [FI] Finland ...................... 941025

[51] Int. Cl.⁶ .......................................... A61B 6/14
[52] U.S. Cl. ........................... 378/168; 378/170; 378/105
[58] Field of Search ......................... 378/168, 169, 378/170, 204, 205, 98.8

[56] References Cited

U.S. PATENT DOCUMENTS

| | | | |
|---|---|---|---|
| 1,657,230 | 1/1928 | Simonton | 378/170 |
| 2,123,210 | 7/1938 | Schantz | 378/170 |
| 2,193,993 | 3/1940 | De Weal | 378/170 |
| 4,295,050 | 10/1981 | Linden | |
| 4,592,084 | 5/1986 | McAuslan | |
| 4,598,416 | 7/1986 | Donato | |
| 4,866,750 | 9/1989 | Chavarria et al. | |
| 4,965,885 | 10/1990 | Fuhrmann | |
| 5,044,009 | 8/1991 | Klauser | |
| 5,090,047 | 2/1992 | Angotti et al. | |
| 5,113,424 | 5/1992 | Burdea et al. | |
| 5,119,410 | 6/1992 | Aonato | |
| 5,289,522 | 2/1994 | Kanbau et al. | |
| 5,473,662 | 12/1995 | Barish | 378/170 |

FOREIGN PATENT DOCUMENTS

| | | |
|---|---|---|
| 0397599 | 11/1990 | European Pat. Off. |
| 708993 | 5/1954 | United Kingdom ............ 378/170 |
| 8403033 | 8/1984 | WIPO |
| 9222188 | 12/1992 | WIPO |

*Primary Examiner*—David P. Porta
*Attorney, Agent, or Firm*—Ladas & Parry

[57] ABSTRACT

Intraoral dental radiography based on X-ray photography. The radiography is performed with either a conventional film or a picture plate, in which case the dimensions of the picture may be corrected by means of a computer program while viewing the picture on a monitor. Problems caused by a shallow palate because of the oblique position of the film holder may thus be eliminated, and the top of the roots of the tooth is also visible in the picture. The picture plate or film holder used in the method comprises three interlinked parts, namely a film holder, a bite portion, and an alignment rod, and one sliding part, i.e. the positioning block.

11 Claims, 2 Drawing Sheets

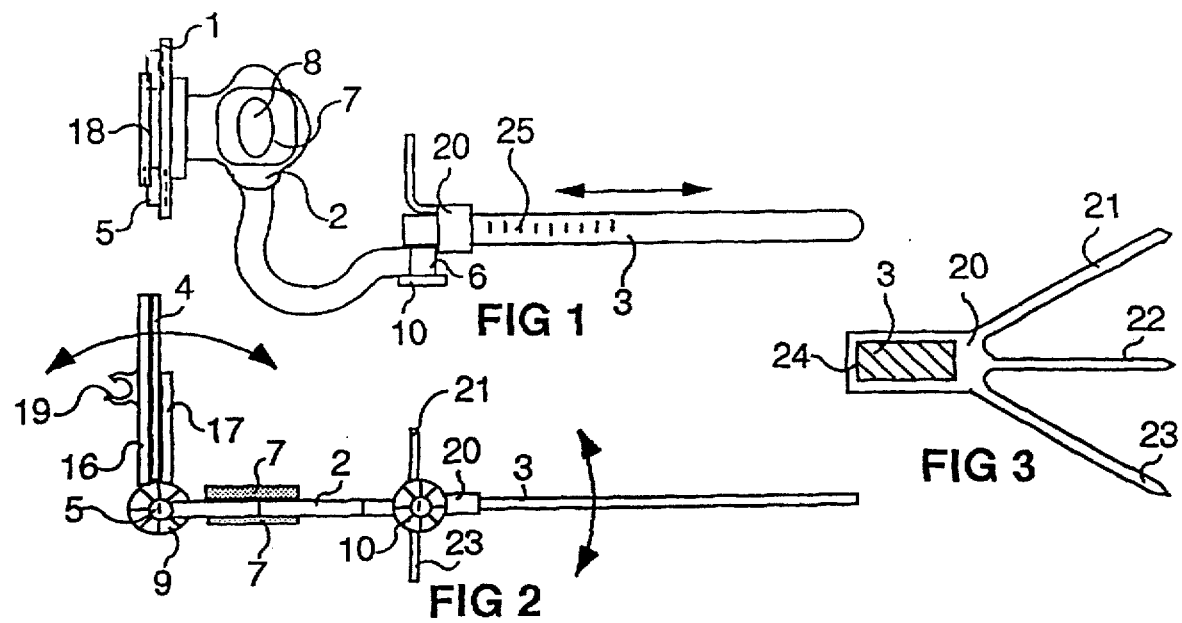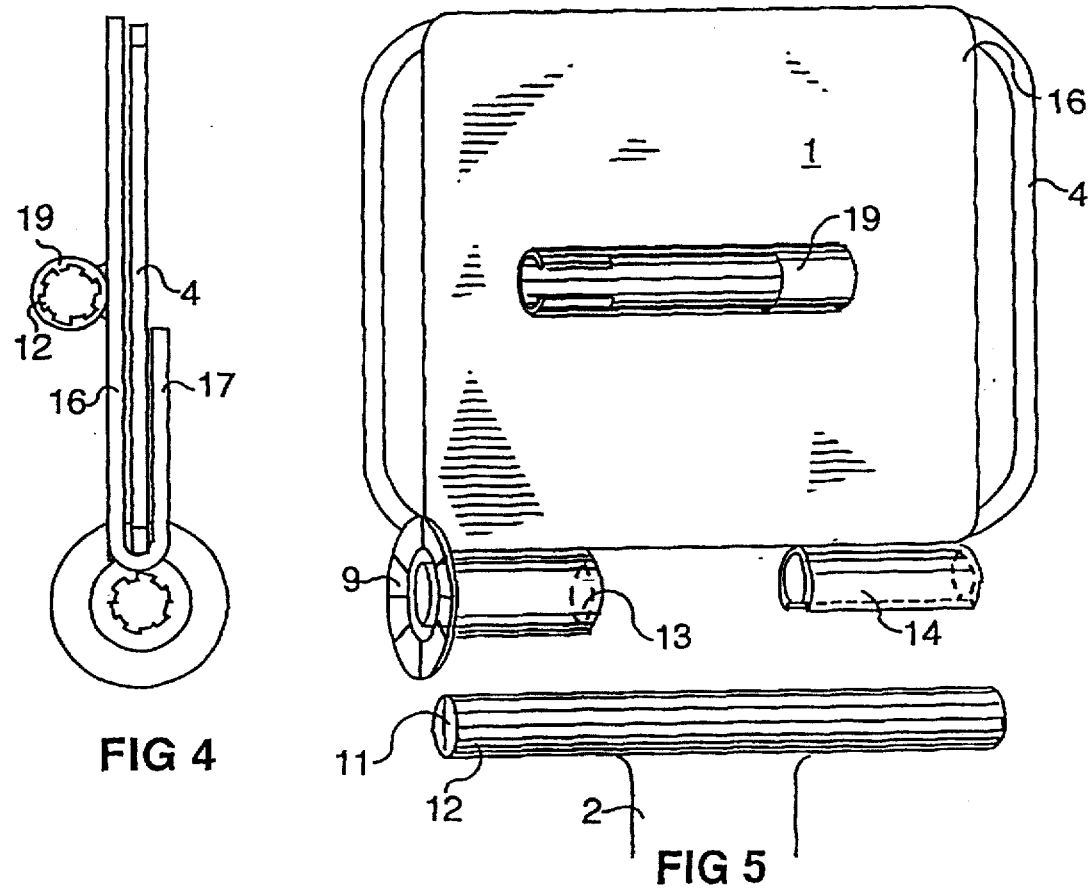

DIGITAL INTRAORAL X-RAY PHOTOGRAPHY METHOD AND HOLDER FOR PICTURE PLATE OR X-RAY FILM

The invention relates to intraoral dental radiography based on X-ray photography. To perform the photography method, a holder for an X-ray film or a digital picture plate comprising a film holder, a bite portion and an alignment rod, is used.

Traditionally dental radiography has been performed on an X-ray film exposed by an X-ray tube. A quite simple holder comprising two positions of which both have usually been perpendicular to the bar of the film holder has generally been used for positioning the X-ray film inside the mouth. The X-ray tube has, as a rule, been aligned by means of the bar. In many cases, X-raying with a holder has proved impossible due to the narrowness of the mouth, the target area, and less developed film holders. Therefore, various solutions involving cotton pads have been applied, whereby the patient presses the X-ray film into the desired position in the mouth. One such case is a shallow palate, which makes it impossible to X-ray especially the dental root tops with existing methods by means of a film holder. In this case the patient holds the film in place with his or her finger against the tooth using cotton pads, and exposure takes place almost at random, wherefore the angle between the film and the X-ray tube is not accurately known. With existing methods, the root tops do not always show on the film, and using finger placement by means of cotton pads easily results in an obscure picture, even if the so-called bisecting angle technique were used, as the angles are not accurately known. Introducing fingers into the mouth and using them as film holders is naturally also unpleasant and unhygienic as far as the patient is concerned.

In conventional X-ray film holders the bar is perpendicular and they have two positions, one for X-raying the roots and the other for so-called bite-wing radiography intended for X-raying the crown parts of opposing teeth. A digital picture plate is not applicable in a conventional film holder, where the slot usually is too small for the picture plate, and its use is essentially limited by the lack of possibilities of changing positions. Naturally, the advantages of modern digital technology and picture processing cannot be utilized when conventional film holders are used or when the film is placed manually. If the angle between the digital picture plate and the X-ray tube is known with reasonable accuracy, the digital picture may be amended on a display screen by a program which is designed for this purpose, and which will take into account the set angles and the distance between the picture plate and the X-ray tube, and will automatically calculate the corrections for the distortions they have caused. Conventional X-raying methods are slow, and the results may not be read until the picture has been developed. A digital picture is immediately readable.

Up to now, one of the problems has also been the difficulty of re-exposing in view of the so-called subtraction technique, as X-raying in exactly the same place and the same position has been problematic. It has also been difficult to X-ray files used in root canal therapy while they are positioned in the canals.

By the method and the holder for a picture plate or X-ray film of the invention, a decisive improvement may be attained over the existing methods.

The digital intraoral X-ray photography method of the invention and the holder for a picture plate or X-ray film applied therein are characterized by that which is set forth in the attached claims.

By means of the new method and device of the invention, intraoral X-raying becomes more hygienic, more reliable, easier and faster. The holder of the invention may be used in nearly all intraoral radiographs, including cases where the so-called cotton pad technique is currently applied. The holder may be used in all intraoral radiographs of the areas of the maxilla and mandible, and in the so-called bite-wing radiography, where the crown parts of upper and lower jaw teeth of the same side are X-rayed simultaneously. When the picture plate photography of the invention is used, applying the so-called bisecting angle technique becomes easier, and by the use of the desired film angle and an accordingly aligned alignment rod, more accurate results are obtained. The measuring scales may be synchronized so that the angle of the X-ray tube, as shown by the indicator rod, complies with the standard values of the bisecting angle technique, whereby the best photographing result is obtained even with conventional dental film techniques. This is especially important in e.g. assessing the length of the root canal in root canal therapy, when the right dimensions are crucial to the success of the therapy. By means of a holder the probability of getting accurate pictures will increase, and the need for re-exposure and the amount of radiation to which a patient is exposed are decreased. This is a more hygienic and pleasant manner of taking radiographs as compared to the cotton pad technique, as the patient has no need to introduce a finger into the mouth. The device of the invention is anatomically designed. The intraoral parts are detachable, allowing easier and more effective sterilization. The film slot accommodates both a dental film and a digital picture plate, which does not usually fit in the prior art devices. Applied to a digital radiographic method, the method of the invention will open new prospects for intraoral radiography. The X-ray tube may be aimed orthogonally to the object, and to a certain limit the film angle may be oblique in relation to the object and still the X-ray pictures will have the right dimensions. This is achieved by a computer utility program which will calculate, on the basis of the given film angle and, if needed, also the angle and distance of the X-ray tube, the right dimensions for the object being X-rayed. The method of the invention also allows precise re-positioning when follow-up exposures are taken. This is achieved by means of bite blocks on top of which impression agent is administered; when solidifying, the agent will retain its form and adhere to the bite block.

In the following the invention will be described in greater detail with reference to the accompanying drawings:

FIG. 1 is a top view of a holder for a picture plate or an X-ray film.

FIG. 2 is a side view of a holder for a picture plate and an X-ray film.

FIG. 3 shows the positioning block of an X-ray tube.

FIG. 4 is an enlarged side view of an X-ray film holder.

FIG. 5 shows the fastening mechanism of a film holder and a bite portion.

Figure 6:
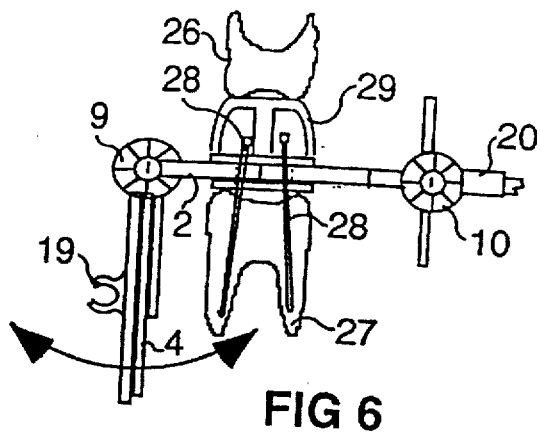
FIG. 6 shows a protective cover to be attached to a bite portion for use in root canal therapy.

In FIGS. 1 to 5, numeral 1 refers to a film holder and numeral 2 to a bite portion, to which an alignment rod 3 is joined. Numeral 4 denotes a film or a picture plate. Joints are denoted by numerals 5 and 6. The bite portion 2 is provided with detachable additional pieces 7. The bite portion 2 comprises a hole 8, whereon additional pieces of the bite portion are attached, and said hole may be used when accommodating root canal files. The angles formed by the joints 5 and 6 are readable on scales 9 and 10. The holder for a picture plate or film 1 is attached to the bite portion by means of an axle 11 comprising grooves 12. The axle 11 is placed into slots 13 and 14, comprising respective grooves 12 on the inside, and to allow installation, one of the slots, i.e. slot 14, has been split. Numeral 16 denotes a back plate and numeral 17 a front plate of the film holder 1. Numeral 18 denotes a slot therebetween. For bite-wing radiography, the back plate 16 of the film holder 1 is provided with a tubular and partly open clamp 19 to facilitate fastening of the axle 11. Numeral 20 refers to a positioning block for the X-ray tube; the positioning block comprises three branches 21, 22, 23, and it slides on the slot 14 along the alignment rod 3.

Figure 7:
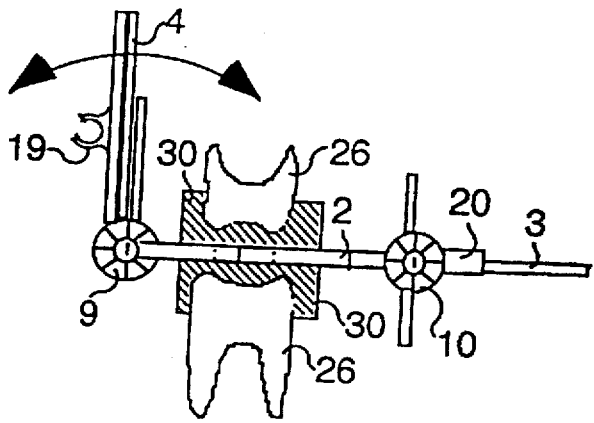
FIG. 7 shows a bite portion used in positioning.

In FIG. 6, numeral 26 refers to a tooth and numeral 27 to its root. Numeral 28 denotes a root canal file and numeral 29 a cover. In FIG. 7, the bite portion 2 comprises bite blocks 30, which are treated with impression agent that will harden for the purpose of re-positioning.

Figure 8:
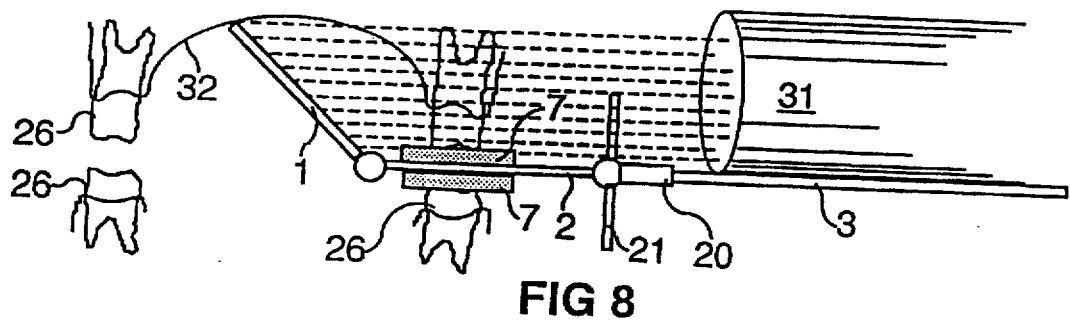
FIG. 8 shows positioning of an X-ray tube and a film holder in a case of new digital X-raying.
Figure 9:
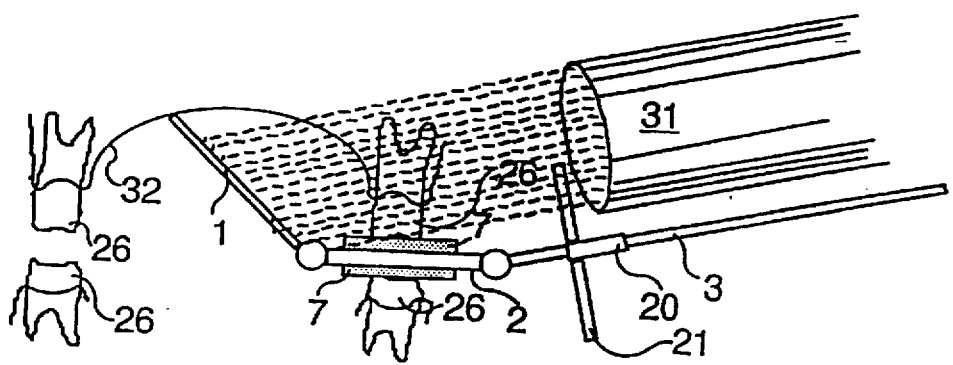
FIG. 9 shows positioning of an X-ray tube and a film holder in radiography using the bisecting angle technique.

FIGS. 8 and 9 schematically show the photography method. Numeral 31 refers to an X-ray tube and numeral 32 to the palate.

When a film holder of the invention is used in conventional dental radiography, the film holder 1 is positioned inside the mouth, and the patient will bite on the additional pieces 7 in the bite portion 2, thus securing the desired position of the holder. Before exposure, the desired angle of the film holder 1 has been set by means of a joint 5, and the width of the angle is readable on a display scale 9. A joint 6, between the bite portion 2 and an alignment rod 3, is provided with a scale 10, by means of which the right angle may be set for the X-ray tube in accordance with the bisecting angle technique. By the use of digital technology and picture processing methods corrected by micro processors, a digital picture plate may, in accordance with the size of the mouth, be placed in a suitable angle to allow the top of the root 27 of a tooth 26 also to show, and the X-ray tube 31 may be positioned perpendicularly to the tooth. With the digital picture plate 4 in an oblique position and the X-ray tube 31 in a straight position, the picture will naturally stretch, but by means of a picture processing program this may be corrected, and thus the resulting picture is similar to the one obtained when X-raying perpendicularly to the film. The conventional bisecting-angle technique may also be used in processing the digital picture if the top edge of the root does not show in the picture when direct radiography is used.

By means of a three-branched positioning block 20, fastened around the alignment rod 3, the X-ray tube 31 may be positioned correctly depending on whether ordinary or bite-wing radiography is used. Additionally, the distance and position of the X-ray tube may be defined by the positioning block 20. The reading is given on a scale 25, and beam dispersion may be taken into account.

The holder of the invention comprises four different parts and additional equipment, of which the film holder 1, is detachable. The film holder 1, the bite portion 2, and the alignment rod 3 are interlinked by joints 5 and 6 comprising scales 9 and 10 for reading of angles, and the X-ray tube positioning block 20 is slidably connected to the alignment rod 3. The joints 5 and 6, and their parts, are indented to allow desired positioning by means of certain angle adjustments. For bite-wing radiography, the back plate 16 of the film holder comprises a clamp 19 allowing perpendicular attachment of the back plate 16 from its middle part to the bite portion 2. The bite portion 2 and its hole 8 are equipped with additional pieces 7 of different thicknesses according to the need. The additional pieces 7 are usually made from bite-resistant, semihard material. The film holder 1 and the bite portion 2 are placed inside the mouth of the patient, and are thus anatomically designed in an optimal way. The film holder 1 with the attached bite portion 2 and the alignment rod 3 are made from non-toxic, roentgen-negative plastics tolerating steam-sterilization, and are thus reusable after sterilization. In case repeated so-called subtraction pictures must be taken of the patients mouth for follow-up, bite blocks 30, disposed within the holes 8 of the bite portion 2, are provided with bite impressions hardened by means of an impression agent, to allow the film holder or picture plate to be placed in its original position by means of the bite impressions. Naturally, the joints 5 and 6 have to be positioned according to the original values of the positions.

In root canal therapy, when root canal files 28 have been used, the problem has been to determine their depth. When a cover 29 mountable on the bite block 2 is used, pictures may be taken relatively easily by means of the film holder and the X-ray tube, and the penetration of the files may be accurately determined.

Naturally, the digital intraoral X-ray photography method of the invention will lead to new applications and facilitate and expand the possibilities of intraoral radiography. The holder for a picture plate or film applied in the method of the invention may naturally assume other forms than those disclosed in this application. Also the structure of the joints attached to the film holder may be different, and the angular scales 8 may be located otherwise than in the embodiment of this application without departing from the scope of the inventive concept.

I claim:

1. In a method for digital or film-based intraoral dental x-ray photography, wherein a holder for a picture plate or film is held in place in the mouth of a patient, and the picture plate or film is placed at a desired angle in relation to a tooth being x-rayed with radiation emitted from an x-ray tube, the improvement comprising the steps of:
    (a) collecting data as to (i) an angle between the picture plate or film and the tooth, (ii) an angle between the x-ray tube and the tooth and (iii) a distance between the x-ray tube and the tooth; and
    (b) correcting an image distortion resulting from a non-orthogonal disposition between said tube and said tooth or between said tube and said picture plate or film based upon the data collected in step (a).

2. A method as claimed in claim 1, comprising displaying an image of the tooth on a display screen of a computer and correcting the image by providing the computer with the data collected in step (a) and with a program that causes the computer to process the data to display the image on the display screen without the image distortion.

3. A method as claimed in claim 1 wherein the holder comprises a bite block and an alignment rod, wherein the data collected in step (a) as to the angle between the picture plate or film and the moth is generated by measuring an angle between the picture plate or film and the bite block, wherein the data collected in step (a) as to the angle between the x-ray tube and the tooth is generated by measuring an angle between the bite block and the alignment rod and wherein the data collected in step (a) as to the distance between the x-ray tube and the tooth is generated by measuring a distance between the x-ray tube and the bite block.

4. A method as claimed in claim 2 wherein the holder comprises a bite block and an alignment rod, wherein the data collected in step (a) as to the angle between the picture plate or film and the tooth is generated by measuring an angle between the picture plate or film and the bite block, wherein the data collected in step (a) as to the angle between the x-ray tube and the tooth is generated by measuring an angle between the bite block and the alignment rod and wherein the data collected in step (a) as to the distance between the x-ray tube and the tooth is generated by measuring a distance between the x-ray tube and the bite block.

5. An apparatus for a picture plate or film used in intraoral x-ray photography of a tooth, comprising a film holder, a bite portion, an alignment rod for aligning an x-ray tube, first joint means for joining the film holder and the bite portion so that they can be adjustably disposed with respect to one another at any of a plurality of angles, second joint means for joining the bite portion and the alignment rod so that they can be adjustably disposed with respect to one another at any of a plurality of angles, scale means for collecting data concerning an angle between the film holder and the bite portion, concerning an angle between the bite portion and the alignment rod, and concerning a distance between the x-ray tube and the tooth, and processing means for processing the data collected by the scale means and for using the processed data to correct for imaging distortions in the x-ray photography.

6. An apparatus as claimed in claim 5, wherein the scale means comprises a plurality of scales and wherein the first and second joint means comprise respective first and second joints, each of said first and second joints comprising an axle and a slot that are grooved, each said joint being provided with one of the plurality of scales.

7. An apparatus as claimed in claim 5, comprising a positioning block for the x-ray tube connected to the alignment rod so as to slide back and forth along it, said positioning block comprising a plurality of branches adapted to function as adjusting points, the alignment rod comprising a scale for providing the processing means with data concerning the distance between the x-ray tube and the tooth.

8. An apparatus as claimed in claim 5, comprising a plurality of additional pieces attached to the bite portion by a hole in the bite portion, said additional pieces providing a spacing between upper and lower teeth of a patient to be treated.

9. An apparatus as claimed in claim 8, wherein the additional pieces comprise bite impressions cured onto the surfaces of the additional pieces with an impression agent, whereby said bite impressions provide an indication as to an original position of the upper and lower teeth in follow-up procedures.

10. An apparatus as claimed in claim 8 comprising a cover attached to a top of the bite position and a root canal file in the hole of the bite portion.

11. An apparatus as claimed in claim 6, wherein the slot of each of said joints has a part that is partially opened to allow for insertion of a respective one of the axles, each slot and axle being grooved to allow for graded adjustment therebetween.

* * * * *